(12) United States Patent
Lin

(10) Patent No.: US 11,607,481 B2
(45) Date of Patent: Mar. 21, 2023

(54) BIDIRECTIONAL VASCULAR CANNULA DEVICE

(71) Applicant: Po-Yen Lin, Kaohsiung (TW)

(72) Inventor: Po-Yen Lin, Kaohsiung (TW)

( * ) Notice: Subject to any disclaimer, the term of this patent is extended or adjusted under 35 U.S.C. 154(b) by 131 days.

(21) Appl. No.: 17/117,297

(22) Filed: Dec. 10, 2020

(65) Prior Publication Data

US 2021/0178048 A1 Jun. 17, 2021

(30) Foreign Application Priority Data

Dec. 11, 2019 (TW) .................................. 108145268

(51) Int. Cl.
*A61M 1/36* (2006.01)
*A61M 39/22* (2006.01)

(52) U.S. Cl.
CPC ........ *A61M 1/3659* (2014.02); *A61M 1/3607* (2014.02); *A61M 39/22* (2013.01)

(58) Field of Classification Search
CPC .. A61M 1/3659; A61M 1/3607; A61M 39/22; A61M 25/0029; A61M 2025/0031; A61M 1/30; A61M 1/3661
See application file for complete search history.

(56) References Cited

U.S. PATENT DOCUMENTS

| 5,171,218 | A | 12/1992 | Fonger et al. | |
|---|---|---|---|---|
| 2004/0267185 | A1* | 12/2004 | Weaver | A61M 39/24 604/6.16 |
| 2012/0109060 | A1* | 5/2012 | Kick | A61M 39/22 604/122 |
| 2012/0259273 | A1* | 10/2012 | Moshinsky | A61M 25/0043 604/28 |
| 2015/0273201 | A1* | 10/2015 | Tallarida | A61M 39/22 604/156 |
| 2016/0121079 | A1 | 5/2016 | Walther et al. | |
| 2016/0296728 | A1* | 10/2016 | Smith | A61M 1/3659 |
| 2018/0043085 | A1 | 2/2018 | Cho | |
| 2019/0314615 | A1* | 10/2019 | Johnson | A61M 25/0606 |
| 2019/0336676 | A1* | 11/2019 | Biller | A61M 25/0074 |
| 2020/0306440 | A1* | 10/2020 | Kon | A61M 25/007 |

FOREIGN PATENT DOCUMENTS

WO WO-2019181042 A1 * 9/2019 ......... A61B 1/00066

* cited by examiner

*Primary Examiner* — Andrew J Mensh
*Assistant Examiner* — Kate Elizabeth Strachan
(74) *Attorney, Agent, or Firm* — Muncy, Geissler, Olds & Lowe, P.C.

(57) ABSTRACT

A bidirectional vascular cannula device includes a tube and a moving mechanism having a through hole. The tube includes a tubular wall which defines therein a passage having opposite proximal and distal opened ends. The tubular wall has a secondary opening formed therethrough. Oxygenated blood infused into the passage from the proximal opened end is delivered to one end of the blood vessel from the distal opened end, and a part of the blood is delivered to the other end of the blood vessel through the secondary opening and the through hole so as to obviate ischemic caused by cannula occlusion. The moving mechanism is operable to be moved to permit a part of the moving mechanism to project outwardly and to be attached to the inner wall of the blood vessel for positioning the cannula device.

4 Claims, 9 Drawing Sheets

BIDIRECTIONAL VASCULAR CANNULA DEVICE

CROSS-REFERENCE TO RELATED APPLICATION

This application claims priority of Taiwanese Patent Application No. 108145268, filed on Dec. 11, 2019.

FIELD

The disclosure relates to a cannula device, and more particularly to a bidirectional vascular cannula device.

BACKGROUND

When an extracorporeal life support system is operated, blood needs to be sent back to the human circulatory system through an external pipeline for physiological functioning. A cannula connected with extracorporeal life support system is typically used to infuse oxygenated blood into the femoral artery in vicinity of the groin region. Currently, a cannula is generally used to supply an adequate amount of blood toward the heart, but occludes the blood vessel and blocks blood flow to the extremity. For patients undergoing extracorporeal life support, problems, such as ischemia of the lower limbs, might occur.

During the insertion of such single-directional cannula, to attempt to solve the ischemia problem of lower limbs caused by arterial cannula occlusion, an additional cannula is used to insert into the blood vessel in which blood flows toward the lower extremity to deliver blood to the lower limbs. However, since the additional cannula, wires, and related hardware equipment and monitoring devices are required, the surgeon needs more time for the cannula insertion.

A bidirectional arterial cannula, as disclosed in U.S. Pat. No. 5,171,218, US 2016/0121079 A1 and US 2018/0043085 A1, is designed to deliver blood in both directions to maintain a flow toward the heart as well as in the direction of the lower extremity, and has a positioning mechanism disposed to position the cannula in the blood vessel. This positioning mechanism is complicated in structure and occupies a great space inside the cannula, hence adversely affecting the amount of fluid flow.

SUMMARY

Therefore, an object of the disclosure is to provide a bidirectional vascular cannula device that can alleviate at least one of the drawbacks of the prior art.

According to the disclosure, the bidirectional vascular cannula device includes a tube and a moving mechanism having a through hole. The tube includes a tubular wall which defines a passage therein. The passage has a proximal opened end and a distal opened end opposite to each other. The tubular wall has an outer wall surface, an inner wall surface radially opposite to outer wall surface, and a secondary opening formed therethrough from the outer wall surface to the inner wall surface and in spatial communication with the passage. The moving mechanism is slidably embedded in the tubular wall between the outer wall surface and the inner wall surface. The through hole is formed adjacent to the secondary opening. The moving mechanism is operable to move relative to the tubular wall between a first position, where the through hole is offset from the secondary opening and the moving mechanism blocks the secondary opening, and a second position, where the through hole is aligned and in spatial communication with the secondary opening and a part of the moving mechanism projects outwardly from the outer wall surface.

Oxygenated blood infused into the passage from the proximal opened end is delivered to one end of the blood vessel from the distal opened end, and a part of the blood is delivered to the other end of the blood vessel through the secondary opening and the through hole so as to obviate ischemia caused by cannula occlusion. Moreover, the moving mechanism is operable to be moved to the second position to permit a part of the moving mechanism to project outwardly and to be attached to the inner wall of the blood vessel for positioning the cannula device.

BRIEF DESCRIPTION OF THE DRAWINGS

Other features and advantages of the disclosure will become apparent in the following detailed description of the embodiments with reference to the accompanying drawings, of which.

DETAILED DESCRIPTION

Figure 1:
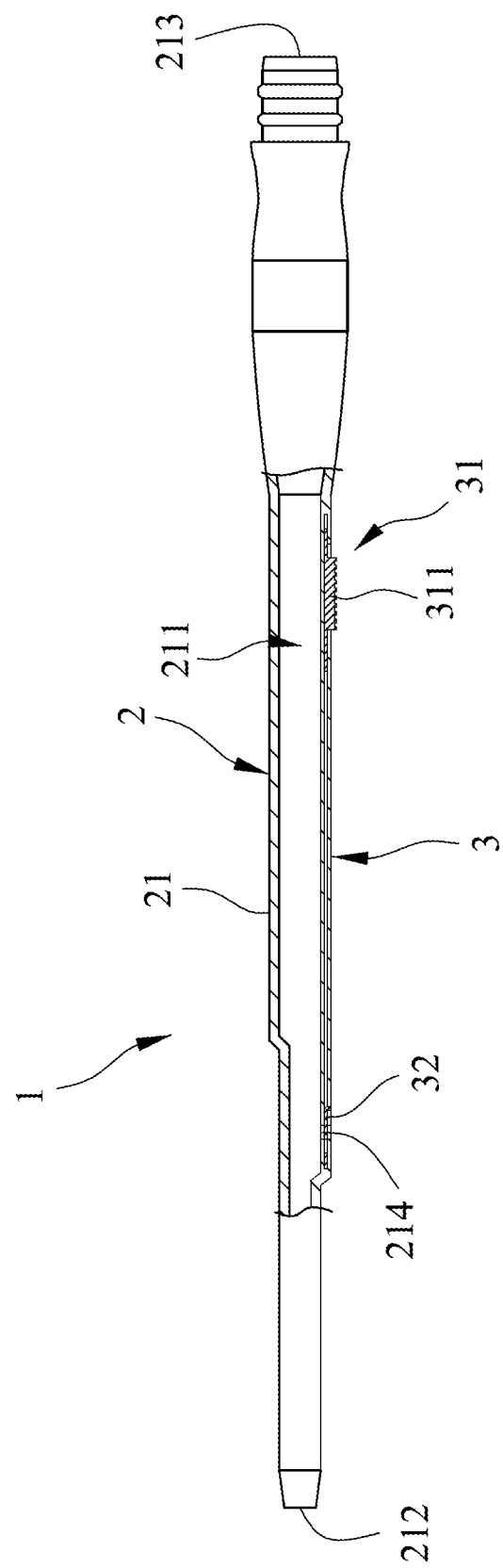
FIG. 1 is a partly sectional side view illustrating a first embodiment of a bidirectional vascular cannula device according to the disclosure.

Before the disclosure is described in greater detail, it should be noted that where considered appropriate, reference numerals or terminal portions of reference numerals have been repeated among the figures to indicate corresponding or analogous elements, which may optionally have similar characteristics.

Figure 2:
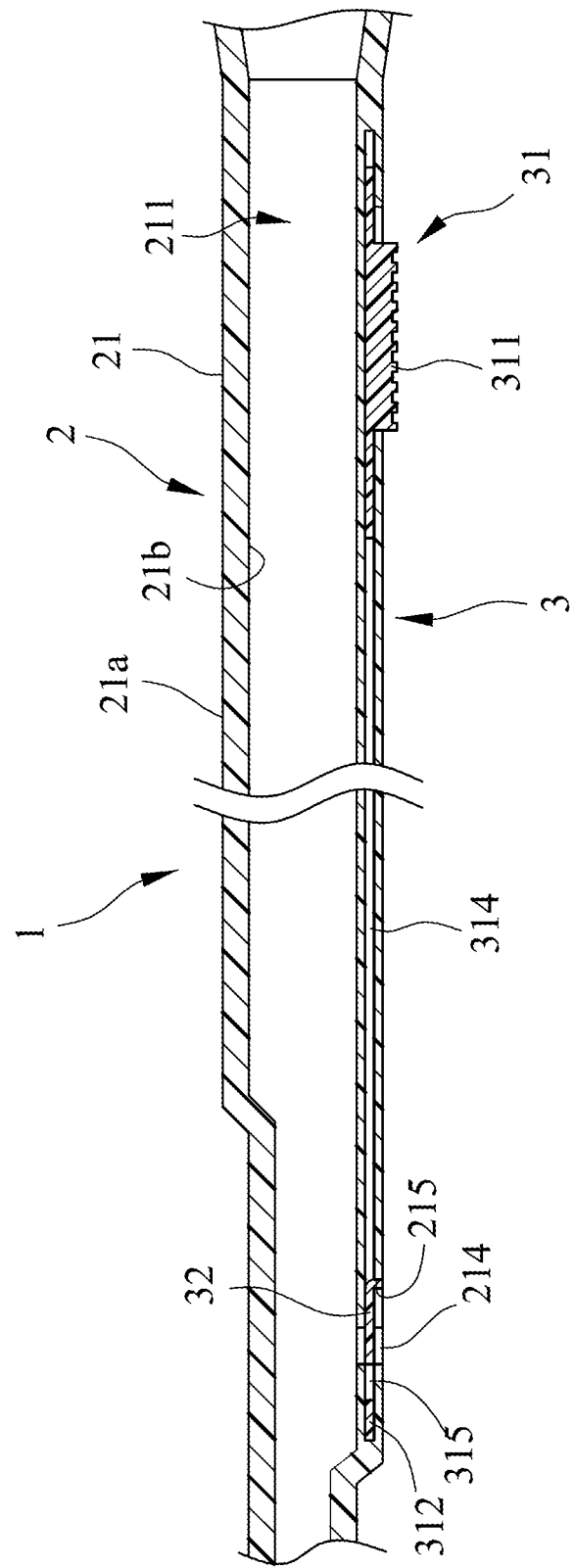
FIG. 2 is a fragmentary sectional view illustrating the first embodiment in a state when a moving mechanism is in a first position.
Figure 3:
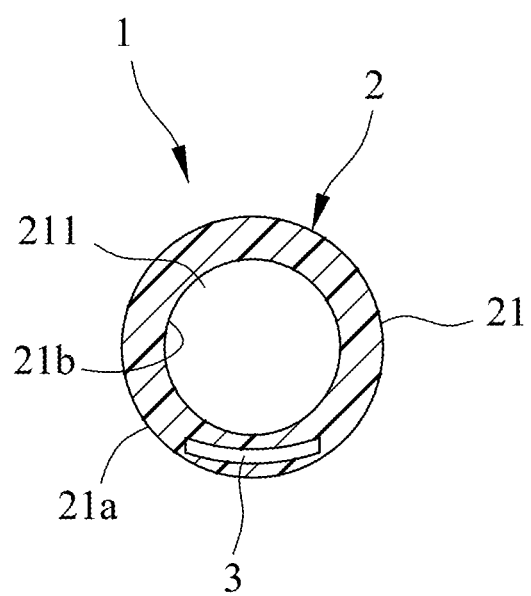
FIG. 3 is a cross-sectional view of the first embodiment.

Referring to FIGS. 1 to 3, a first embodiment of a bidirectional vascular cannula device 1 according to the disclosure includes a flexible tube 2 and a moving mechanism 3 disposed to the tube 2. The tube 2 includes a flexible tubular wall 21 which defines a passage 211 therein. The passage 211 has a proximal opened end 213 and a distal opened end 212 opposite to each other in a longitudinal direction. The tubular wall 21 has an outer wall surface (21a), an inner wall surface (21b) radially opposite to outer wall surface (21a), a secondary opening 214 formed therethrough from the outer wall surface (21a) to the inner wall surface (21b) and in spatial communication with the passage 211, and a slit 215 formed therethrough and interposed between the proximal opened end 213 and the secondary opening 214 in the longitudinal direction.

Figure 4:
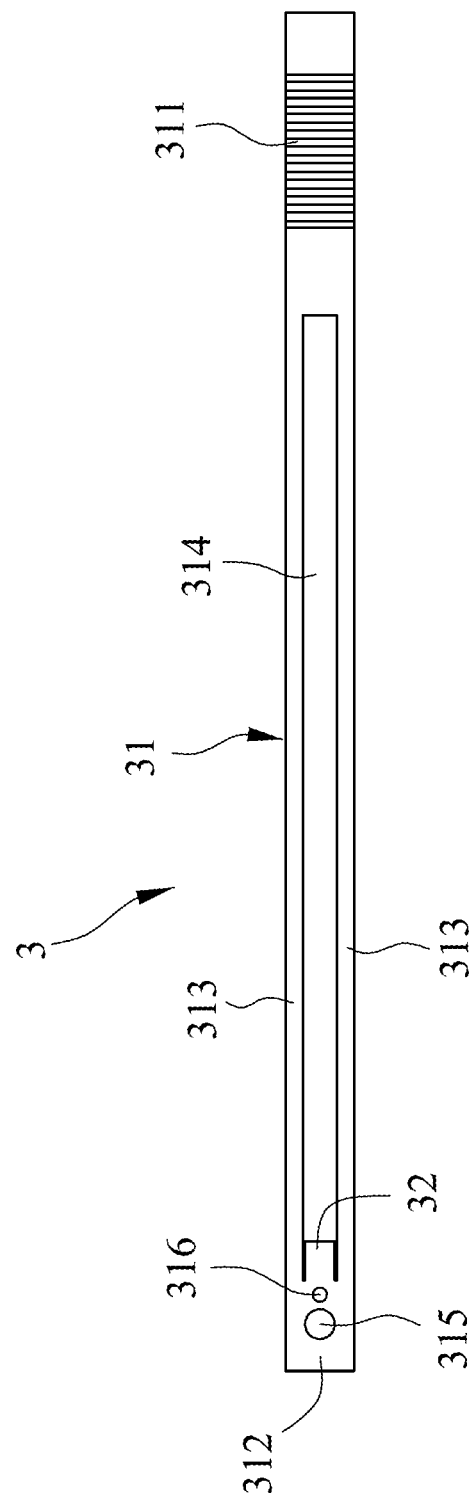
FIG. 4 is a schematic top view of the moving mechanism of the first embodiment.

With reference to FIGS. 1, 2 and 4, the moving mechanism 3 includes a slider 31 which is embedded in the tubular wall 21 between the outer wall surface (21a) and the inner wall surface (21b) and slidable relative to the tubular wall 21 in the longitudinal direction, and a flexible tongue plate 32 which is connected with the slider 31. The slider 31 extends in the longitudinal direction, and has an operating portion 311 which is disposed proximate to the proximal opened end 213 of the tube 2 and which partially projects outwardly of the outer wall surface (21a), an end plate portion 312 which is disposed proximate to the distal opened end 212, and two longitudinal connecting portions 313 each of which extends in the longitudinal direction and interconnects the operating portion 311 and the end plate portion 312. The operating portion 311, the end plate portion 312 and the longitudinal connecting portions 313 cooperatively define a notched slot 314 thereamong. The end plate portion 312 has a through hole 315 and a flash hole 316 (see FIG. 4) which is formed therethrough and interposed between the notched slot 314 and the through hole 315. An end of the tongue plate 32 is integrally formed and connected with the end plate portion 312.

Figure 5:
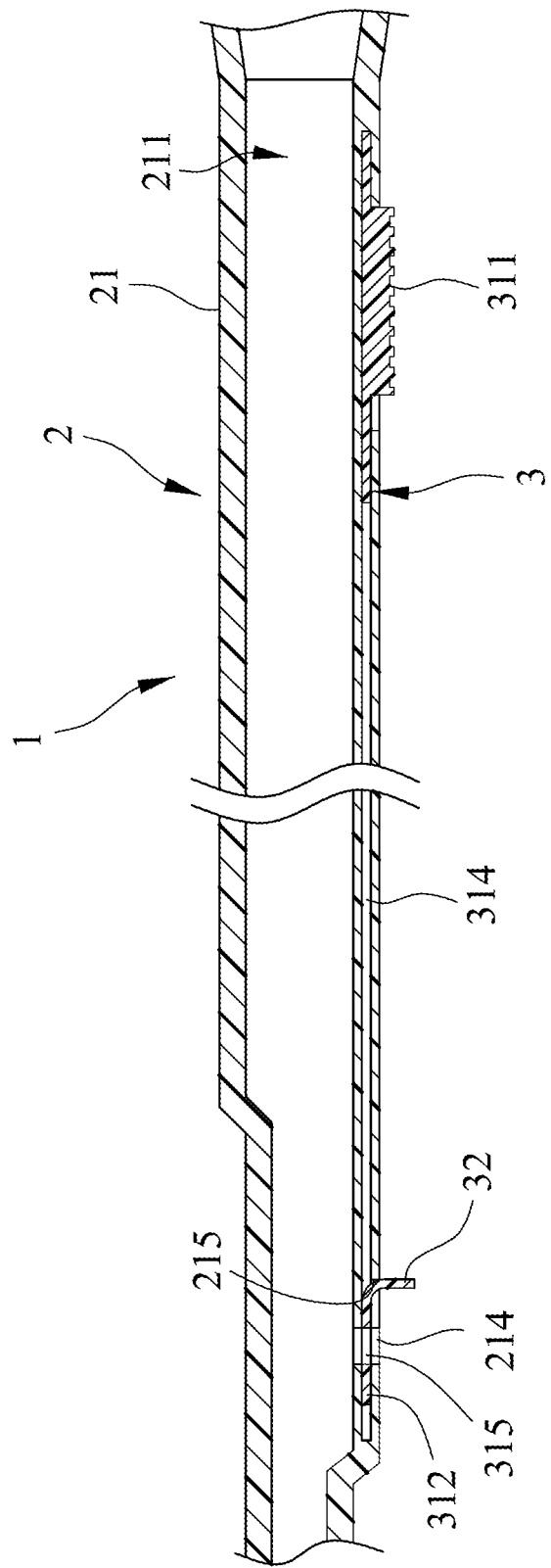
FIG. 5 is a fragmentary sectional view illustrating the first embodiment in a state when the moving mechanism is in a second position.

With reference to FIGS. 2, 4 and 5, the moving mechanism 3 is operable by an operator through the operating portion 311 to move relative to the tubular wall 21 between a first position (as shown in FIG. 2) and a second position (as shown in FIG. 5). In the first position, the flash hole 316 is aligned and in spatial communication with the secondary opening 214, and the through hole 315 is offset from the secondary opening 214 such that the moving mechanism 3 substantially blocks the secondary opening 214. Further, the tongue plate 32 is suspended in the notched slot 314. With the movement of the slider 31 toward the proximal opened end 213 (see FIG. 1), the moving mechanism 3 is moved to the second position. During this movement, the tongue plate 32 is moved by the slider 31 and bent elastically to protrude outwardly of the tubular wall 21 through the slit 215. When the moving mechanism 3 is in the second position, the flash hole 316 is offset from the secondary opening 214, and the through hole 315 is aligned and in spatial communication with the secondary opening 214.

Figure 6A:
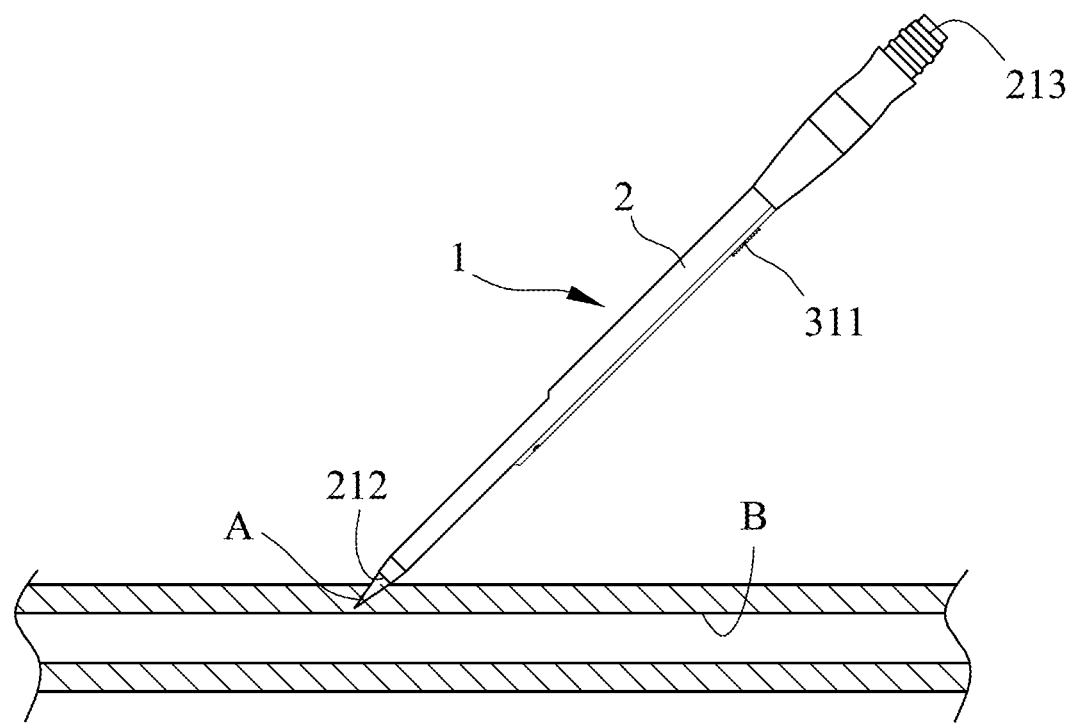
FIGS. 6A-6B are schematic views illustrating the first embodiment deployed in a patient's blood vessel.
Figure 6B:
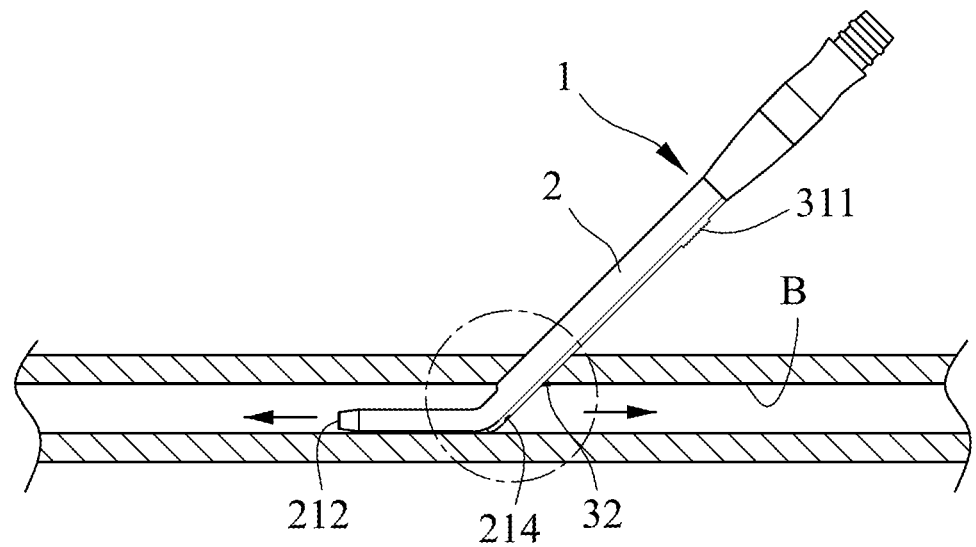
Figure 7:
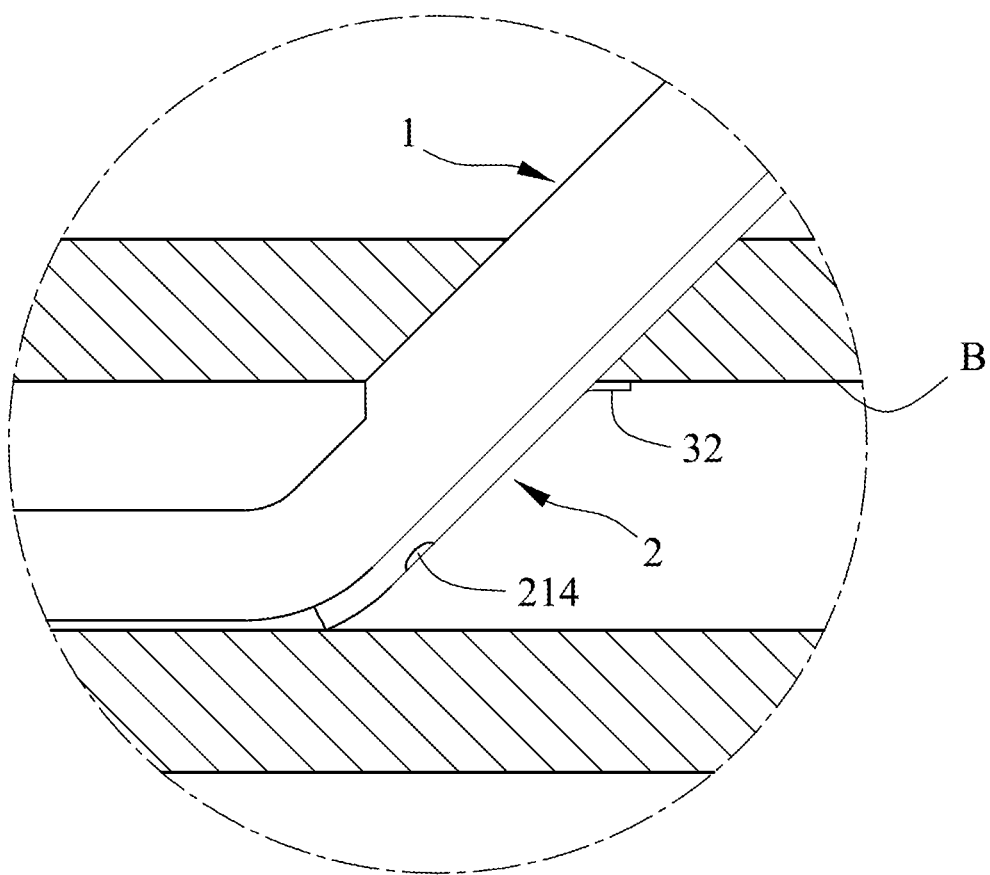
FIG. 7 is an enlarged view illustrating the first embodiment when a flexible tongue plate projects to abut against an inner wall of the blood vessel.

With reference to FIGS. 2, 6A-6B and 7, the cannula device 1 of this embodiment is used with a stiffer dilator (A) to be inserted into a blood vessel (B). The dilator (A) is positioned inside the tube 2 from the proximal opened end 213 and encloses the distal opened end 212. At this stage shown in FIG. 6A, the moving mechanism 3 is in the first position, where the tongue plate 32 is received in the notched slot 314 to keep the outer wall surface (21a) smooth for facilitating sliding movement of the cannula device inside the patient's body. When the flash hole 316 (see FIG. 4) enters the blood vessel (B), blood enters the passage 211 from the flash hole 316 and through the secondary opening 214 to provide a visual indication in the tube 2. With reference to FIGS. 5, 6B and 7, subsequently, the operating portion 311 is operated to move the moving mechanism 3 to the second position. The tongue plate 32 projects from the tube 31 to abut against the inner wall of the blood vessel (B) so as to position the tube 2 in the blood vessel (B) for preventing undesired movement. Finally, the dilator (A) is removed from the cannula device 1. Oxygenated blood infused into the passage 211 from the proximal opened end 213 is delivered to one end of the blood vessel (B) from the distal opened end 212, and a part of the blood is delivered to the other end of the blood vessel (B) through the secondary opening 214 and the through hole 315 so as to obviate ischemia caused by cannula occlusion to remote end blood flow.

Figure 8:
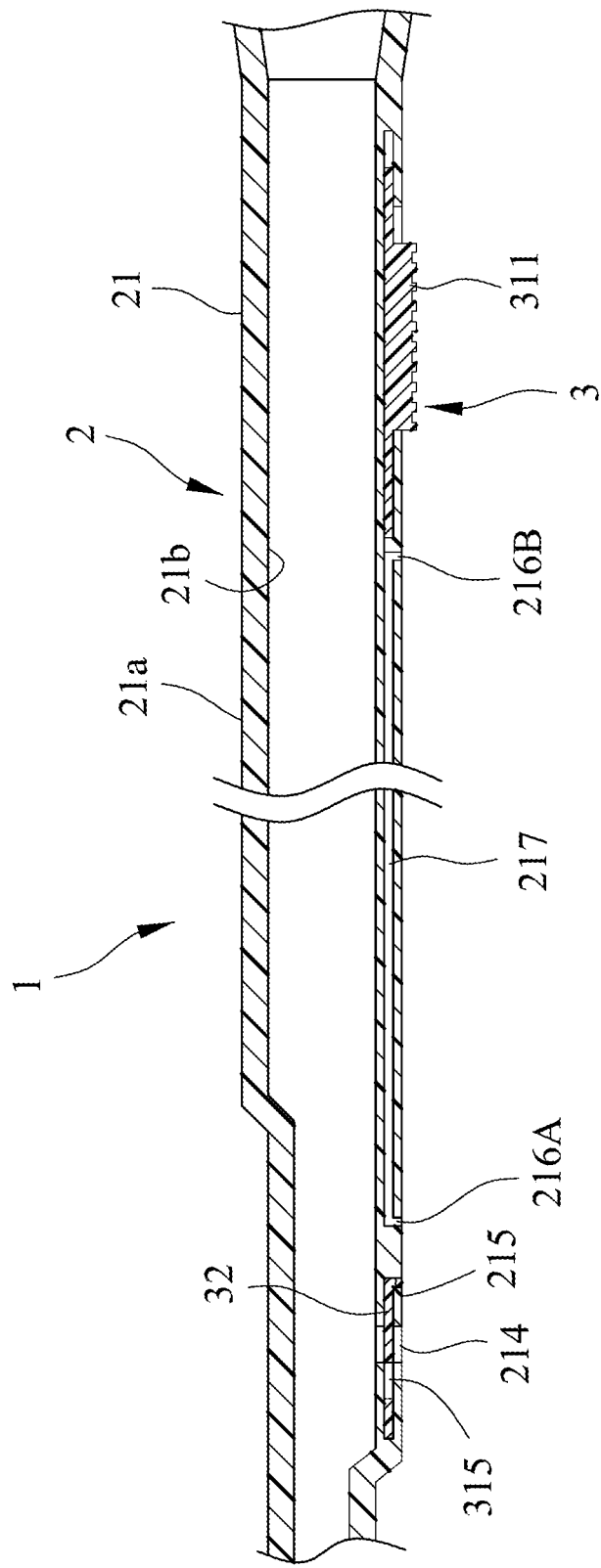
FIG. 8 is a fragmentary sectional view illustrating a second embodiment of the bidirectional vascular cannula device according to the disclosure.
Figure 9:
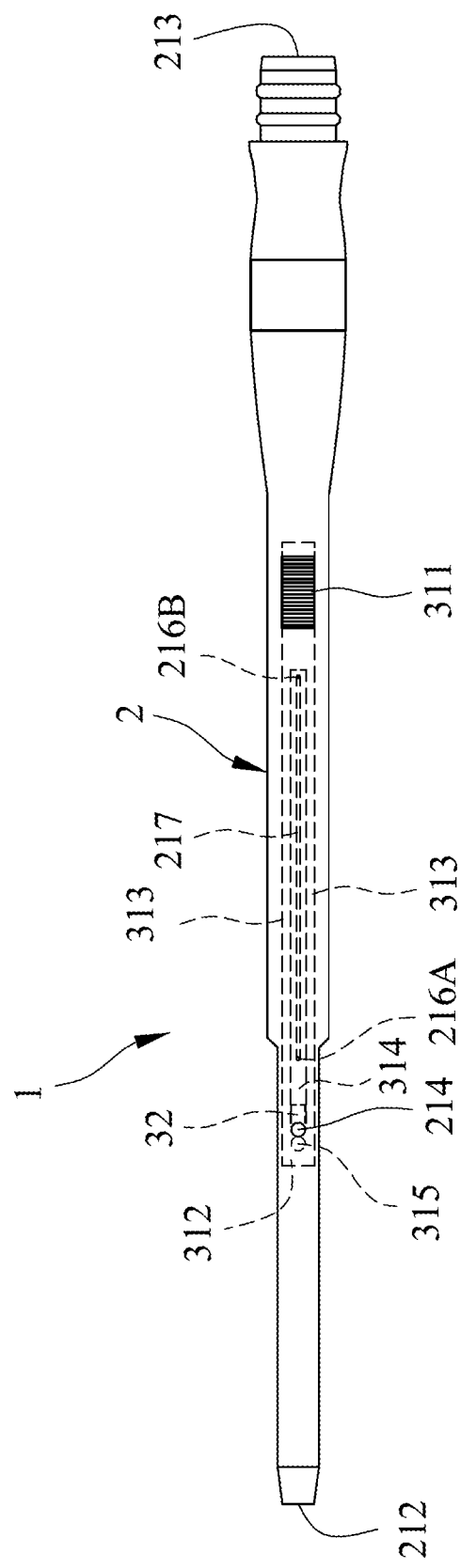
FIG. 9 is a schematic top view of the second embodiment.

Referring to FIGS. 8 and 9, in a second embodiment, instead of having the flash hole 316 (see FIG. 4) formed in the endplate portion 312 of the slider 31, the tubular wall 21 of the tube 2 has a thin flash chamber 217 which is formed therein and between the outer and inner wall surfaces (21a, 21b) and which extends in the longitudinal direction to terminate at an inlet port (216A) that is adjacent to the secondary opening 214, and an outlet port (216B) that is proximate to the proximal opened end 213. When the moving mechanism 3 of this embodiment is in the first position, the end plate portion 312 blocks the secondary opening 214 and the communication between the through hole 315 and the secondary opening 214 is interrupted. When the moving mechanism 3 is moved to the second position, the through hole 315 is aligned and in spatial communication with the secondary opening 214. During the cannula insertion, blood enters the flash chamber 217 from the inlet port (216A) and flows out through the outlet port (216B), which provides a visual indication in the flash chamber 217 so as to render the operation precise and rapid.

As illustrated, with the secondary opening 214 through which a part of blood is delivered to the opposite direction of the blood vessel (B), such as to the lower extremity away from the heart, the ischemia caused by cannula occlusion is prevented. With the flexible tongue plate 32 which is movable to project from the tube 2 to be attached to the inner wall of blood vessel (B), a stable and firm position of the cannula device 1 in a patient's body is obtained. Meanwhile, a blood visual indication is provided during the cannula insertion.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A bidirectional vascular cannula device comprising:
   a tube including a tubular wall which defines a passage therein, said passage having a proximal opened end and a distal opened end opposite to each other, said tubular wall having an outer wall surface, an inner wall surface radially opposite to said outer wall surface, and a secondary opening formed therethrough from said outer wall surface to said inner wall surface and in spatial communication with said passage, said tubular wall having a slit formed therethrough and interposed between said proximal opened end and said distal opened end in a longitudinal direction; and
   a moving mechanism slidably embedded in said tubular wall between said outer wall surface and said inner wall surface, said moving mechanism including a slider which is embedded in and slidable relative to said tubular wall in the longitudinal direction and which has a through hole adjacent to said secondary opening, and a flexible tongue plate which is connected with said slider, said moving mechanism being operable to move relative to said tubular wall between a first position, where said through hole is offset from said secondary opening and said moving mechanism blocks said secondary opening and said tongue plate is disposed in said tubular wall, and a second position, where said through hole is aligned and in spatial communication with said secondary opening and said tongue plate is deformed and projects outwardly of said outer wall surface through said slit.

2. The bidirectional vascular cannula device as claimed in claim 1, wherein said slider has an operating portion which is disposed proximate to said proximal opened end and which partially projects outwardly of said outer wall surface, an end plate portion which is disposed proximate to said distal opened end, and two longitudinal connecting portions each of which extends in the longitudinal direction and interconnects said operating portion and said end plate portion, said end plate portion having said through hole, and being integrally formed and connected with said tongue plate, said operating portion, said end plate portion and said longitudinal connecting portions cooperatively defining a notched slot, said tongue plate being suspended in said notched slot when said moving mechanism is in the first position, and being bent elastically and moved to protrude outwardly of said tubular wall when said moving mechanism is moved to the second position.

3. The bidirectional vascular cannula device as claimed in claim 2, wherein said end plate portion of said slider has a guiding hole formed therethrough and interposed between said notched slot and said through hole, said guiding hole being aligned and in spatial communication with said secondary opening when said moving mechanism is in the first position, and being offset from said secondary opening when said moving mechanism is in the second position.

4. The bidirectional vascular cannula device as claimed in claim 2, wherein said tubular wall has a flash chamber which is formed therein and which extends in the longitudinal direction to terminate at an inlet port that is adjacent to said secondary opening, and an outlet port that is proximate to said proximal opened end.

\* \* \* \* \*